(12) United States Patent
Inoguchi et al.

(10) Patent No.: US 10,821,126 B2
(45) Date of Patent: Nov. 3, 2020

(54) AGENT FOR TREATING RETINOPATHY

(71) Applicant: CARNA HEALTH SUPPORT LTD., Fukuoka (JP)

(72) Inventors: Toyoshi Inoguchi, Fukuoka (JP); Yasutaka Maeda, Fukuoka (JP); Toshinobu Maki, Fukuoka (JP); Noriyuki Sonoda, Fukuoka (JP)

(73) Assignee: CARNA HEALTH SUPPORT LTD., Fukuoka (JP)

(*) Notice: Subject to any disclaimer, the term of this patent is extended or adjusted under 35 U.S.C. 154(b) by 34 days.

(21) Appl. No.: 16/327,649

(22) PCT Filed: Dec. 9, 2016

(86) PCT No.: PCT/JP2016/086658
§ 371 (c)(1),
(2) Date: Feb. 22, 2019

(87) PCT Pub. No.: WO2018/037581
PCT Pub. Date: Mar. 1, 2018

(65) Prior Publication Data
US 2019/0240243 A1 Aug. 8, 2019

(30) Foreign Application Priority Data
Aug. 26, 2016 (JP) .................. 2016-165656

(51) Int. Cl.
| | | |
|---|---|---|
| *A61K 31/7028* | (2006.01) | |
| *A61P 27/02* | (2006.01) | |
| *A61P 3/10* | (2006.01) | |
| *A61K 45/00* | (2006.01) | |
| *A61K 31/382* | (2006.01) | |
| *A61K 31/70* | (2006.01) | |
| *A61K 31/7042* | (2006.01) | |
| *A61K 31/7048* | (2006.01) | |

(52) U.S. Cl.
CPC ........ *A61K 31/7028* (2013.01); *A61K 31/382* (2013.01); *A61K 31/70* (2013.01); *A61K 31/7042* (2013.01); *A61K 31/7048* (2013.01); *A61K 45/00* (2013.01); *A61P 3/10* (2018.01); *A61P 27/02* (2018.01)

(58) Field of Classification Search
None
See application file for complete search history.

(56) References Cited

U.S. PATENT DOCUMENTS

| | | | |
|---|---|---|---|
| 2016/0113953 A1* | 4/2016 | Gannedahl | A61K 45/06 514/35 |
| 2018/0104268 A1* | 4/2018 | Mayoux | A61K 31/7048 |

OTHER PUBLICATIONS

Bailey, "Renal glucose reabsorption inhibitors to treat diabetes", Trends in Pharmacological Sciences, vol. 32, No. 2, Feb. 2011, pp. 63-71.
Zaccardi et al., "Efficacy and safety of sodium-glucose co-transporter-2 inhibitors in type 2 diabetes mellitus: systematic review and network meta-analysis", Diabetes, Obesity and Metabolism, Aug. 2016, vol. 18, pp. 783-794.
Takakura et al., "Effect of ipragliflozin, an SGLT2 inhibitor, on progression of diabetic microvascular complications in spontaneously diabetic Torii fatty rats", Life Sciences, Jan. 2016, vol. 147, pp. 125-131.
Takahashi et al., "Luseogliflozin(TS-071), a Novel, Potent and Selective SGLT2 Inhibitor, Prevents Diabetic Retinopathy in Rats", Diabetes, Jun. 2012, vol. 61, Issue Supplemental 1, p. A279, col. 1082-P.
Dziuba et al., "Modeling Macrovascular and Microvascular Outcomes of the SGLT-2 Inhibitor Dapagliflozin vs Standard of Care in Second-Line Diabetes Therapy", Diabetes, Jul. 2013, vol. 62, Issue Supplement 1, 2013, p. A672, col. 2641-P0.
International Search Report in English issued in PCT/JP2016/086658, dated Feb. 28, 2017.
International Preliminary Report on Patentability in English issued in PCT/JP2016/086658, dated Feb. 28, 2019.

* cited by examiner

*Primary Examiner* — Shaojia A Jiang
(74) *Attorney, Agent, or Firm* — Greenblum & Bernstein, P.L.C.

(57) ABSTRACT

It is to provide an agent for treating and/or ameliorating retinopathy caused by glucose. It is an agent for treating retinopathy caused by glucose comprising sodium/glucose cotransporter2 inhibitor (SGLT2 inhibitor) as an active ingredient, and is used at a normal dosage amount, or at a lower dosage whereby no lowering in blood sugar is observed.

11 Claims, 4 Drawing Sheets

[Figure 1]
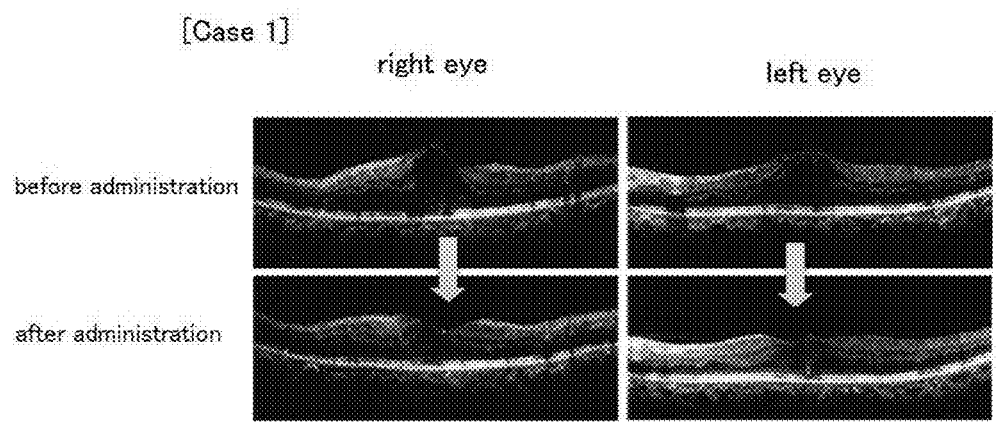
[Figure 2]
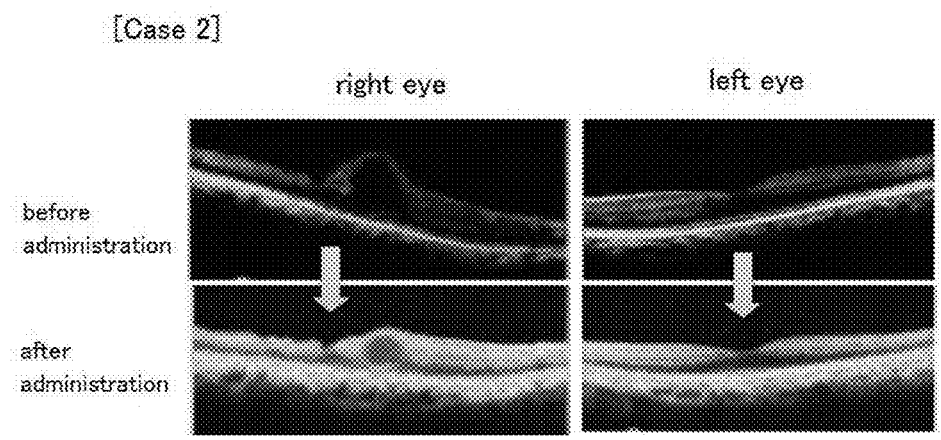

[Figure 3]
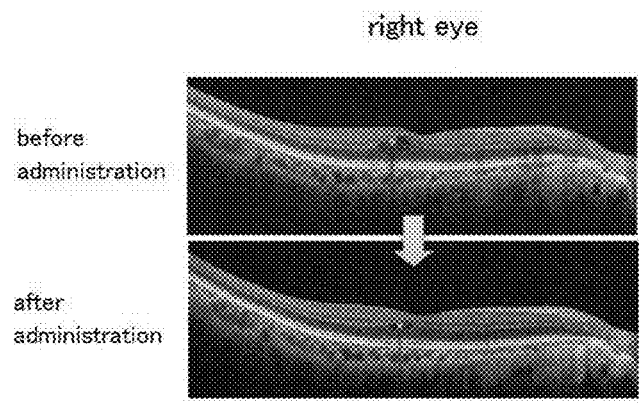
[Figure 4]
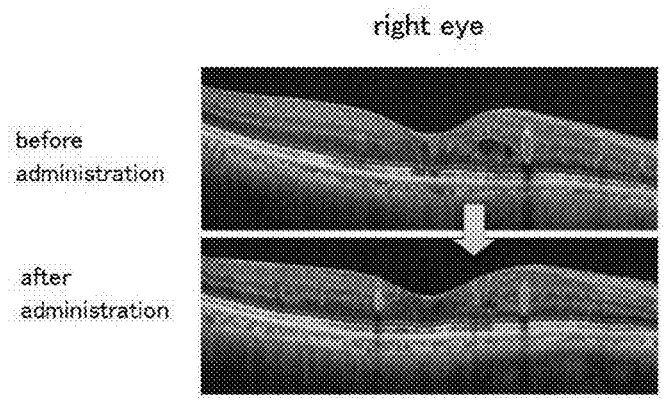

[Figure 5]
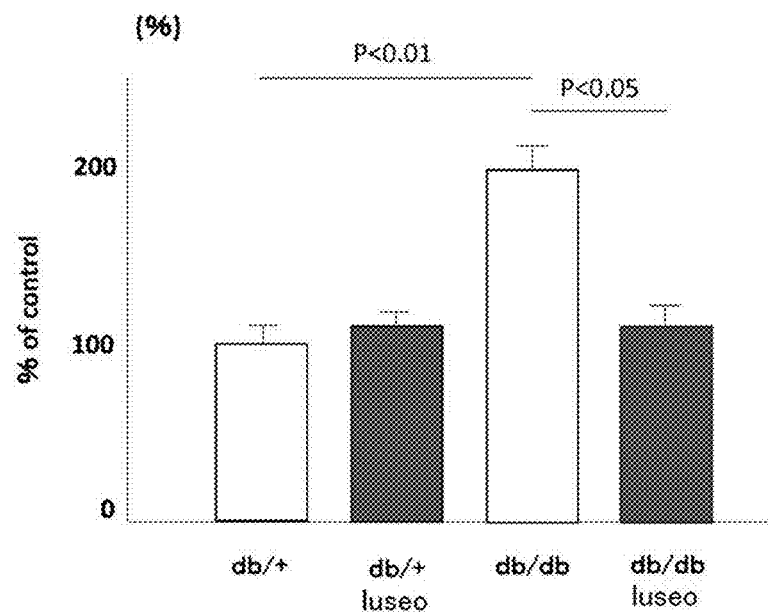
[Figure 6]
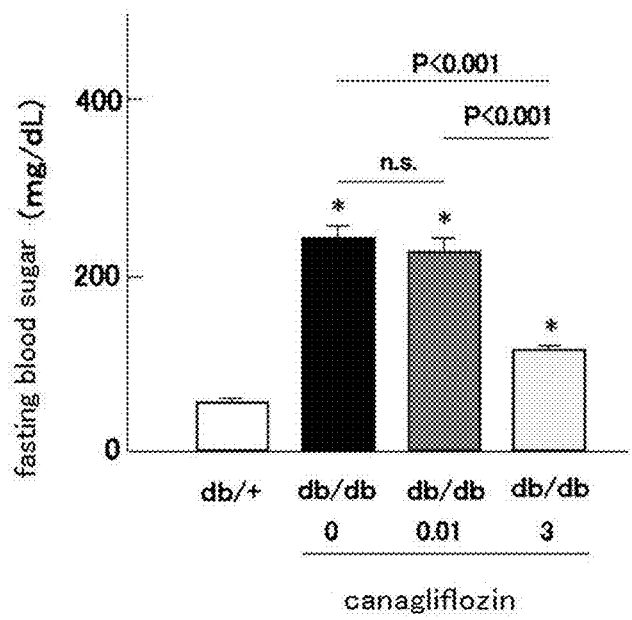

[Figure 7]
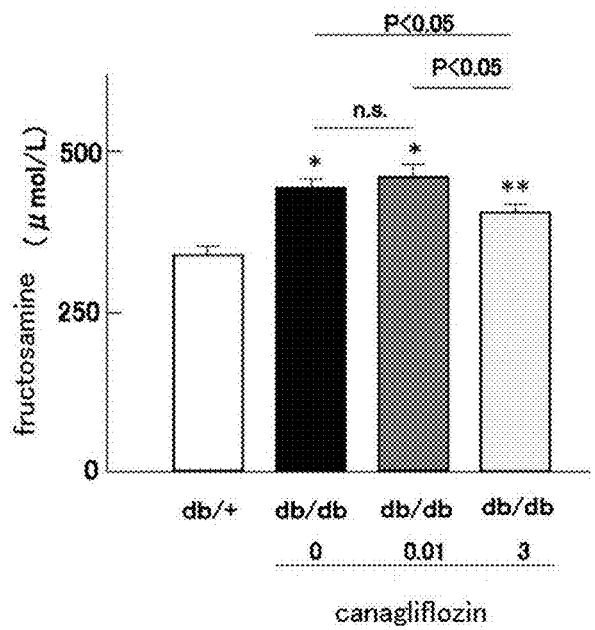
[Figure 8]
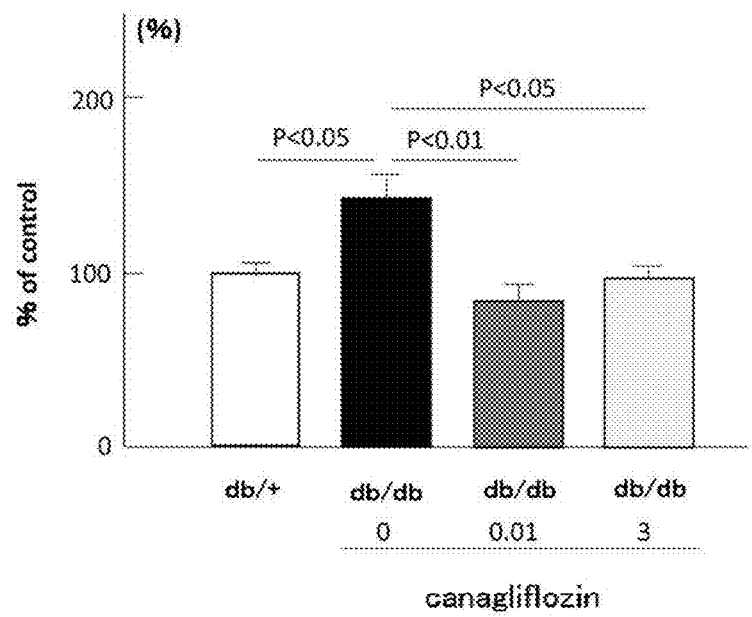

AGENT FOR TREATING RETINOPATHY

TECHNICAL FIELD

The present invention relates to an agent for treating retinopathy caused by glucose.

BACKGROUND ART

Diabetic retinopathy is the second causative disease of acquired blindness. Decrease in vision caused by macular edema etc. developed from various stages of the retinopathy is the cause that significantly decreases the QOL of many patients. As ophthalmologic treatment for retinopathy, photocoagulation therapy or vitreous surgery is performed for severe cases of retinopathy, and this medical treatment is an effective treatment from the point of view of prevention of blindness. Further, for macular edema, intraocular injection of steroid or anti-VEGF antibody is performed, and this medical treatment is a temporary effective treatment.

However, specific oral therapeutic agent that suppresses progression or exacerbation of retinopathy, or oral therapeutic agent that ameliorates macular edema is not present at the moment, and the development is strongly awaited.

On the other hand, SGLT2 inhibitor agent is a therapeutic agent for diabetes that inhibits sodium/glucose cotransporter2 (SGLT2) that is specifically present in proximal renal tubules and performs reabsorption of glucose, and promotes glucose excretion from urine to show an antihyperglycemic action. Clinical application of six types of SGLT2 inhibitor agent has already been performed (see for example, non-patent references 1, 2). However, it is not known that the SGLT2 inhibitor agent has a direct ameliorating effect on retinal function abnormality.

PRIOR ART DOCUMENTS

Non-Patent Documents

Non Patent Document 1:
Bailey C J. Renal glucose reabsorption inhibitors to treat diabetes. Trends Pharmacil Sci 2011; 32:63-71
Non Patent Document 2:
Zaccadi F, Webb D R, Htike Z Z, Youssef D, Khunti K, Davies M J. Efficacy and safety of sodium-glucose co-transporter-2 inhibitors in type 2 diabetes mellitus: systematic review and network meta-analysis. Diab Obes Metab 2016; 18:783-94

SUMMARY OF THE INVENTION

Object to be Solved by the Invention

The object of the present invention is to provide an agent for treating and/or ameliorating retinopathy caused by glucose.

Means to Solve the Object

The present inventors made a keen study on action effect of SGLT2 inhibitor agent as a therapeutic agent for diabetes showing antihyperglycemic action. First, the present inventors focused that with respect to the actual dosage amount of SGLT2 inhibitor agent, only a tiny amount reaches the proximal renal tubules where the SGLT2 inhibitor agent acts. The present inventors further advanced their studies, and found out that the existing SGLT2 inhibitor agent has an effect of ameliorating retinal function abnormality caused by glucose, not only with a normal dosage amount but also with a low dosage administration which does not show an antihyperglycemic action.

Specifically, it has been found out that SGLT2 inhibitor agent can ameliorate retinal function abnormality caused by glucose, by a mechanism that does not mediate at all antihyperglycemic action. The present invention has been thus completed.

Specifically, the present invention relates to the following.
[1] An agent for treating retinopathy caused by glucose, comprising sodium/glucose cotransporter2 inhibitor (SGLT2 inhibitor) as an active ingredient.
[2] The agent for treating according to [1], wherein the agent is used by being administered at a low dosage whereby no lowering in blood sugar is observed.
[3] The agent for treating according to [1] or [2], wherein the SGLT2 inhibitor is at least one selected from canagliflozin, ipragliflozin, dapagliflozin, luseogliflozin, empagliflozin and tofogliflozin.
[4] The agent for treating according to any one of [1] to [3], wherein the retinopathy caused by glucose is diabetic retinopathy and/or diabetic macular edema.

Effect of the Invention

According to the therapeutic agent of the present invention, retinopathy caused by glucose can be treated not only with a normal dosage amount, but also by being administered at a low dosage which has no antihyperglycemic action. As the therapeutic agent of the present invention exerts an effect with an administration at a low dosage, there is no problem of hypoglycemia, excessive urination/frequent urination, anhydration, urinary tract infection/genital infection, and increase of ketone body, which are main side effects caused by action of promoting urine sugar elimination of the existing SGLT2 inhibitors, and the safety is significantly high. The therapeutic agent of the present invention enables to expand a new application as a therapeutic agent for diabetic retinopathy, diabetic macular edema, etc.

BRIEF EXPLANATION OF DRAWINGS

FIG. 1 shows the optical coherence tomography (OCT) images before and after the administration of the therapeutic agent of the present invention (existing SGLT2 inhibitor agent) in case 1.

FIG. 2 shows the optical coherence tomography (OCT) images before and after the administration of the therapeutic agent of the present invention (existing SGLT2 inhibitor agent) in case 2.

FIG. 3 shows the optical coherence tomography (OCT) images before and after the administration of the therapeutic agent of the present invention (existing SGLT2 inhibitor agent) in case 3.

FIG. 4 shows the optical coherence tomography (OCT) images before and after the administration of the therapeutic agent of the present invention (existing SGLT2 inhibitor agent) in case 4.

FIG. 5 is a graph showing the ameliorating effect of luseogliflozin administration on increase of retinal vascular permeability in spontaneous type 2 diabetes model db/db mouse.

"db/+" represents control db/+ mouse (n=8), and "db/+ luseo" represents the 10 mg luseogliflozin-administered group of control db/+ mouse. "db/db" represents luseogliflozin non-administered group (n=8) of db/db mouse, and "db/db luseo" represents the 10 mg luseogliflozin-administered group (n=8) of db/db mouse.

FIG. 6 is a graph showing the effect of canagliflozin administration on fasting blood sugar level of type 2 diabetes model db/db mouse.

"db/+" represents control db/+ mouse (n=10), and "db/db" represents spontaneous type 2 diabetes mouse. "db/db 0" represents db/db mouse (n=10) not administered with canagliflozin, and "db/db 0.01" represents db/db mouse (n=10) administered with 0.01 mg/kg/day of canagliflozin. "db/db 3" represents db/db mouse (n=10) administered with 3 mg/kg/day of canagliflozin. "*" represents P<0.001 vs db/+ mouse, and "n.s." denotes no significant difference.

FIG. 7 is a graph showing the effect of canagliflozin administration on fructosamine of type 2 diabetes model db/db mouse.

"db/+" represents control db/+ mouse (n=10), and "db/db" represents spontaneous type 2 diabetes mouse. "db/db 0" represents db/db mouse (n=10) not administered with canagliflozin, and "db/db 0.01" represents db/db mouse (n=10) administered with 0.01 mg/kg/day of canagliflozin. "db/db 3" represents db/db mouse (n=10) administered with 3 mg/kg/day of canagliflozin. "*" represents P<0.001 vs db/+ mouse, "*" represents P<0.01 vs db/+ mouse, and "n.s." denotes no significant difference.

FIG. 8 is a graph showing the ameliorating effect of canagliflozin administration on increase of retinal vascular permeability of spontaneous type 2 diabetes model db/db mouse.

"db/+" represents control db/+ mouse (n=4), "db/db 0" represents db/db mouse (n=4) not administered with canagliflozin, "db/db 0.01" represents db/db mouse (n=4) administered with 0.01 mg/kg/day of canagliflozin. "db/db 3" represents db/db mouse (n=4) administered with 3 mg/kg/day of canagliflozin.

MODE OF CARRYING OUT THE INVENTION

The therapeutic agent of the present invention is an agent for treating retinopathy caused by glucose, and is characterized to comprise SGLT2 inhibitor as an active ingredient.

The present invention has found out that the SGLT2 inhibitor agent which is a hypoglycemic agent targeting kidney has an action of ameliorating retinal function abnormality to which is thought that the agent does not directly act. Showing an action of ameliorating retinal function abnormality even at a low dosage with which no antihyperglycemic action is observed at all, shows that the effect does not mediate antihyperglycemic action.

The retinopathy caused by glucose being the subject of the therapeutic agent of the present invention is not particularly limited as long as it is a disease of retina associated with excessive inflow of glucose into retinal constituent cells. Examples include diabetic retinopathy, diabetic macular edema, senile maculopathy, etc.

The SGLT2 inhibitor in the therapeutic agent of the present invention is not particularly limited as long as it binds to SGLT2 and shows an antagonistic inhibitory effect to glucose intake SGLT2, and is for example a substance having an action of lowering blood sugar by inhibiting SGLT2 present in proximal renal tubules.

Examples of SGLT2 inhibitors include canagliflozin, ipragliflozin, dapagliflozin, luseogliflozin, empagliflozin, tofogliflozin, etc. Specific examples include canagliflozin hydrate ($C_{24}H_{25}FO_5S \cdot \frac{1}{2}H_2O$), ipragliflozin L-proline ($C_{21}H_{21}FO_5S \cdot C_5H_9NO_2$), dapagliflozin propylene glycol hydrate ($C_{21}H_{25}ClO_6 \cdot C_3H_8O_2 \cdot H_2O$), luseogliflozin hydrate ($C_{23}H_{30}O_6S \cdot xH_2O$), empagliflozin ($C_{23}H_{27}ClO_7$), tofogliflozin hydrate ($C_{22}H_{26}O_6 \cdot H_2O$), etc., which are active ingredients of existing SGLT2 inhibitor agents.

As in the above, in the present invention, for example the term "canagliflozin" relates to a compound having the following canagliflozin structure, and includes a pharmaceutical acceptable hydrate, alcohol adduct, amino acid adduct, etc. It is the same for other SGLT2 inhibitors such as "ipragliflozin", etc.

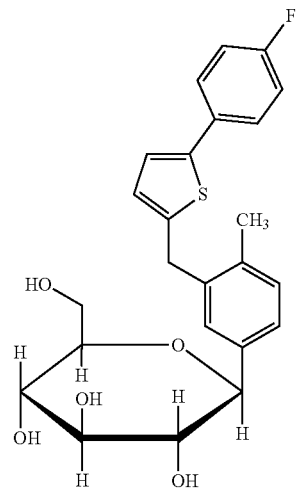

The dosage amount of the therapeutic agent of the present invention can be a amount showing an antihyperglycemic action, or can be a lower dosage. Specifically, the therapeutic agent of the present invention can be used to be administered at a low dosage with which no lowering in blood sugar is observed. As an embodiment of the therapeutic agent of the present invention, for example, an embodiment comprising an active ingredient at a low dosage with which no lowering in blood sugar is observed in a formulation to be administered at once can be exemplified.

The therapeutic agent of the present invention can ameliorate retinal function abnormality by a mechanism that does not mediate antihyperglycemic action at all, and can exerts its effect even with a low dosage showing no antihyperglycemic action. Specifically, the therapeutic agent of the present invention shows an effect of ameliorating retinal function abnormality by reaching an effective concentration that inhibits SGLT2 of retinal constituting cells in blood or in retinal tissues even by being administered at a low dosage that does not reach an effective concentration in urine for SGLT2 suppression.

The low dosage that does not show an antihyperglycemic action in the present invention is an amount by which blood sugar does not significantly decrease, and for example, in case of active ingredients of hypoglycemic agent in which SGLT2 inhibitor is authorized, it means a dosage lower than the authorized minimum dosage amount. The lower limit can be appropriately determined within the range with which an effect is exerted, and for example, for canagliflozin hydrate, it is approximately $\frac{1}{100}$ of the authorized minimum dosage amount. For ipragliflozin L-proline, the maximum blood concentration (Cmax) in the minimum dosage amount is similar with that of canagliflozin, and as the $IC_{50}$ level showing the inhibition activity is also similar, it is similarly approximately $\frac{1}{100}$ of the authorized minimum dosage amount. In case of dapagliflozin propylene glycol hydrate, luseogliflozin hydrate, empagliflozin, tofogliflozin hydrates, as the maximum blood concentration (Cmax) in the minimum dosage amount is approximately 1/10 of that of canagliflozin, while the $IC_{50}$ level is similar, it is approximately 1/10.

Specifically, for canagliflozin hydrate which is authorized as a hypoglycemic agent, it is less than 100 mg per day for an adult (as canagliflozin), and it can be 90 mg or less, 70 mg or less, 50 mg or less, 30 mg or less, 10 mg or less, 5 mg or less, and the lower limit is approximately 1 mg.

For ipragliflozin L-proline, it is less than 50 mg per day for an adult (as ipragliflozin), and it can be 40 mg or less, 30 mg or less, 20 mg or less, 10 mg or less, 5 mg or less, 1 mg or less, and the lower limit is approximately 0.5 mg.

For dapagliflozin propylene glycol hydrate, it is less than 5 mg per day for an adult (as dapagliflozin), and it can be 4 mg or less, 3 mg or less, 2 mg or less, 1 mg or less, and the lower limit is approximately 0.5 mg.

For luseogliflozin hydrate, it is less than 2.5 mg per day for an adult (as luseogliflozin), and it can be 2 mg or less, 1.5 mg or less, 1 mg or less, 0.5 mg or less, and the lower limit is approximately 0.25 mg.

For empagliflozin, it is less than 10 mg per day for an adult, and it can be 9 mg or less, 6 mg or less, 4 mg or less, 2 mg or less, and the lower limit is approximately 0.1 mg.

For tofogliflozin hydrate, it is less than 20 mg per day for an adult (as tofogliflozin), and it can be 18 mg or less, 15 mg or less, 10 mg or less, 5 mg or less, and the lower limit is approximately 2 mg.

The dosage form of the therapeutic agent of the present invention includes a dosage form for oral administration, for injection, for ocular instillation and for intraocular injection, etc., while it is preferred to be oral administration, similar as the existing SGLT2 inhibitor agent (hypoglycemic agent). Further, the form of the therapeutic agent of the present invention include various forms such as tablets, granules, powder, capsules, and liquid.

Further, as a method for treating retinopathy caused by glucose using the therapeutic agent of the present invention, it is not particularly limited as long as it is a method of administrating the therapeutic agent of the present invention comprising SGLT2 inhibitor as an active ingredient to a patient, and preferably is a method of administrating at a dosage whereby no lowering in blood sugar is observed. As it is stated in the above, examples of the administration method include oral administration, administration by injection, ocular instillation and intraocular injection, etc. The details of the therapeutic agent of the present invention and its dosage, and specific examples of retinopathy being the subject of treatment, etc. are as stated in the above.

Example 1

To four cases of diabetic retinopathy having macular edema to which conventional intraocular injection of steroid or anti-VEGF antibody was not effective, the therapeutic agent of the present invention (existing SGLT2 inhibitor) was administered at a normal dosage amount or at a lower dosage amount, and the effect was confirmed. Specifically, for the three cases using dapagliflozin and one case using canagliflozin, the effect was confirmed by assessment using optical coherence tomography (OCT).
[Case 1]
60 years-old, female; suffering from type 2 diabetes, accompanied with proliferative retinopathy in both eyes, and macular edema in both eyes. Steroid sub-tenon injection was frequently performed but was treatment-resistant.

Dapagliflozin propylene glycol hydrate tablet was administered in a half amount of the normal dosage amount (2.5 mg/day as dapagliflozin).
[Case 2]
74 years-old, male; suffering from type 2 diabetes, accompanied with proliferative retinopathy in both eyes, and macular edema in both eyes. Steroid sub-tenon injection was performed but was treatment-resistant.

Canagliflozin hydrate tablet was administered at a normal dosage amount (100 mg/day as canagliflozin).
[Case 3]
68 years-old, female; suffering from type 2 diabetes, accompanied with simple diabetic retinopathy in both eyes, and macular edema in right eye.

Dapagliflozin propylene glycol hydrate tablet was administered in a half amount of the normal dosage amount (2.5 mg/day as dapagliflozin).
[Case 4]
78 years-old, male; suffering from type 2 diabetes, accompanied with preproliferative diabetic retinopathy in both eyes, and macular edema in right eye. Steroid intraocular injection was performed to right eye macular edema, but was resistant.

Dapagliflozin propylene glycol hydrate tablet was administered in a half amount of the normal dosage amount (2.5 mg/day as dapagliflozin).

The results of the above-mentioned four cases 1-4 are shown in FIGS. 1-4, respectively.
[Case 1]
As shown in FIG. 1, about one month after initiation of administration of dapagliflozin propylene glycol hydrate tablet, decrease of macular retinal thickness, cyst reduction, and amelioration of laminar structure were confirmed by OCT. HbA1 before and after administration was 6.7 to 6.6, and blood sugar control did not change. As for the vision, right eye was ameliorated from 0.7 to 0.8, and the left eye did not change, maintaining 1.2.
[Case 2]
As shown in FIG. 2, about 5 months after initiation of administration of canagliflozin hydrate tablet, decrease of macular retinal thickness, cyst reduction, and significant amelioration of laminar structure were confirmed by OCT. HbA1 was 8.0 before administration, which changed to 8.4, 8.1, 7.8 after administration, and there was no change in blood sugar control. The vision was ameliorated in the right eye from 0.4 to 0.5, and in the left eye from 0.7 to 1.2.
[Case 3]
As shown in FIG. 3, in about 4 weeks from initiation of administration of dapagliflozin propylene glycol hydrate tablet, decrease of macular retinal thickness and cyst reduction were confirmed by OCT. HbA1c was ameliorated from 8.7 to 8.0. The vision was ameliorated from 0.15 to 0.2.
[Case 4]
As shown in FIG. 4, in about 4 weeks from initiation of administration of dapagliflozin propylene glycol hydrate tablet, cyst reduction was confirmed by OCT. There was no change in HbA1c, which was 5.9 to 6.1%. The vision was 0.1, and did not change due to severe retinopathy.

As in the above, a significant amelioration effect in macular edema was observed in four cases. In three out of the four cases, no change in blood sugar control state was observed (no lowering in blood sugar was observed) before and after administration, and it was confirmed that the amelioration effect in macular edema was not due to the amelioration of blood sugar control.

Example 2

Subsequently, the amelioration effect on diabetic retinal function (amelioration effect on permeability increase which is a representative abnormality of diabetic retinal vessels) by the therapeutic agent of the present invention (existing SGLT2 inhibitor agent) was confirmed by using spontaneous type 2 diabetes model db/db mouse.

[Normal Dosage (Luseogliflozin)]

Since 8 weeks after birth of spontaneous type 2 diabetes model db/db mouse, a dosage amount (10 mg/kg/day as luseogliflozin) of luseogliflozin hydrate which is an existing SGLT2 inhibitor agent, with which an antihyperglycemic action is confirmed in mouse was orally administered. Two weeks after administration of SGLT2 inhibitor agent, the mouse was euthanized, and all blood vessels were sufficiently refluxed with 10 ml of phosphate buffer solution (PBS), and the eyeballs were extracted. After isolating retina, the albumin amount in the retinal tissues leaked from the blood vessels was measured by western blott method, to assess the vascular permeability increase. The albumin amount in retina was corrected with 3 actin, and is shown by % control by using control db/+ mouse as a standard. The results are shown in FIG. 5.

As shown in FIG. 5, the albumin amount of type 2 diabetes model db/db mouse retina was significantly increased as compared to the control group, and increase of retinal vascular permeability was shown. Further, with the dosage amount of 10 mg/kg/day of luseogliflozin with which an antihyperglycemic action is confirmed in mouse, the increase of retinal albumin amount in type 2 diabetes db/db mouse was significantly ameliorated to the control group level, and the function ameliorating effect on increase of retinal vascular permeability was shown.

[Normal Dosage and Low Dosage Amount (Canagliflozin)]

Next, similarly as for luseogliflozin, the function improvement on increase of retinal vascular permeability was assessed using canagliflozin. Canagliflozin hydrate which is an existing SGLT2 inhibitor agent was orally administered for 2 weeks, at a dosage amount (3 mg/kg/day as canagliflozin) with which an antihyperglycemic action is confirmed in mouse, and at a low dosage (0.01 mg/kg/day as canagliflozin) not showing an antihyperglycemic action.

The above-mentioned low dosage (0.01 mg/kg/day as canagliflozin) not showing an antihyperglycemic action was confirmed by the following method.

To a spontaneous type 2 diabetes model db/db mouse, since 12 weeks after birth, the existing SGLT2 inhibitor agent, canagliflozin hydrate, was orally administered for 2 weeks as canagliflozin, in an amount of 3, 1, 0.1, 0.01, 0.001 mg/kg/day. Effects on body weight, feed intake, urine volume and blood sugar were confirmed.

As a result, with any of the dosage amount of canagliflozin hydrate, no significant change was observed in body weight, feed intake, and urine volume. With an administration of 3.1 mg/kg/day, the fructosamine level which is an index for fasting blood sugar and average blood sugar levels was significantly decreased as compared with the non-administered group, but no significant decrease was observed in blood sugar with an administration of 0.1, 0.01, 0.001 mg/kg/day.

FIGS. 6 and 7 show the results of fructosamine level which is an index for fasting blood sugar and average blood sugar levels when administering 3 mg/kg/day and 0.01 mg/kg/day of canagliflozin hydrate.

As it is shown in FIGS. 6 and 7, the fructosamine level which is an index for fasting blood sugar and average blood sugar levels was significantly decreased in the 3 mg/kg/day-administered group as compared to the non-administered group, while no significant blood sugar decrease was observed with 0.01 mg/kg/day. As shown in FIG. 8, increase of retinal albumin amount was significantly ameliorated to the control group level, in both 3 mg/kg/day-administered group and 0.01 mg/kg/day-administered group of canagliflozin hydrate, and the function improving effect on increase of retinal vascular permeability was confirmed.

As a cause of retinopathy, excessive inflow of glucose into retina constituent cells due to hyperglycemia and various metabolic abnormalities in cells caused by the same (activation of protein kinase, increase of oxidative stress, accumulation of glycation end product AGE, etc.) are estimated.

Particularly, function abnormality of pericyte (perithelium) due to hyperglycemia is considered to be an early disease state of retinopathy, and is considered to be important as a cause of retinopathy as inducing abnormalities in blood-flow control of retinal vessels, vascularization, and vascular endothelia cell permeability. Further, increase of vascular permeability is also thought to be the cause of macular edema. The above-mentioned results show that the SGLT2 inhibitor agent ameliorates increase of vascular permeability of diabetic retinopathy, and it is thought that it suppresses the excessive inflow of glucose into retinal pericyte due to hyperglycemia, and ameliorates abnormalities in pericyte function derived from hyperglycemia.

As it is stated in the above, the therapeutic agent of the present invention (existing SGLT2 inhibitor agent) has been revealed to have an effect of ameliorating diabetic retinal function abnormality both with a normal dosage amount having an antihyperglycemic action, and with a low dosage whereby no lowering in blood sugar is observed.

INDUSTRIAL APPLICABILITY

The therapeutic agent of the present invention enables an enlargement of new application as a therapeutic agent for diabetic retinopathy, diabetic macular edema, etc. and industrial applicability is high.

The invention claimed is:

1. A method for treating retinopathy caused by glucose, comprising administering to a patient in need thereof a composition containing sodium/glucose co-transporter2 inhibitor (SGLT2 inhibitor) as an active ingredient, wherein the SGLT2 inhibitor is administered at a dosage so that no lowering in blood sugar is observed upon administration, and wherein the SGLT2 inhibitor is at least one selected from canagliflozin, ipragliflozin, dapagliflozin, luseogliflozin, empagliflozin and tofogliflozin.

2. The method according to claim 1, wherein the administration is oral administration.

3. The method according to claim 1, wherein the retinopathy caused by glucose is diabetic retinopathy and/or diabetic macular edema.

4. A method for treating retinopathy caused by glucose, comprising administering to a patient in need thereof a composition containing sodium/glucose co-transporter2 inhibitor (SGLT2 inhibitor) as an active ingredient, wherein the SGLT2 inhibitor is administered at a dosage so that no lowering in blood sugar is observed upon administration, and wherein the SGLT2 inhibitor comprises at least one of, as canagliflozin, at a therapeutic dose of less than 100 mg per day; as ipragliflozin, at a therapeutic dose of less than 50 mg per day; as dapagliflozin, at a therapeutic dose of less than 5 mg per day; as luseogliflozin, at a therapeutic dose of less than 2.5 mg per day; as empagliflozin, at a therapeutic dose of less than 10 mg per day; and, as tofogliflozin, at a therapeutic dose of less than 20 mg per day.

5. The method according to claim 4, wherein the administration is oral administration.

6. The method according to claim 4, wherein the retinopathy caused by glucose is diabetic retinopathy and/or diabetic macular edema.

7. A method for treating a patient having retinopathy caused by glucose, comprising administering to the patient a composition containing sodium/glucose co-transporter2 inhibitor (SGLT2 inhibitor) as an active ingredient, to therapeutically treat the retinopathy caused by glucose without showing an antihyperglycemic action, and wherein the SGLT2 inhibitor is at least one selected from canagliflozin, ipragliflozin, dapagliflozin, luseogliflozin, empagliflozin and tofogliflozin.

8. A method for treating a patient having retinopathy caused by glucose, comprising administering to the patient a composition containing sodium/glucose co-transporter2 inhibitor (SGLT2 inhibitor) as an active ingredient, to therapeutically treat the retinopathy caused by glucose without showing an antihyperglycemic action, wherein the retinopathy caused by glucose is diabetic retinopathy and/or diabetic macular edema, and wherein the SGLT2 inhibitor is at least one selected from canagliflozin, ipragliflozin, dapagliflozin, luseogliflozin, empagliflozin and tofogliflozin.

9. The method according to claim 7, wherein the administration is oral administration.

10. The method according to claim 7, wherein the retinopathy caused by glucose is diabetic retinopathy.

11. The method according to claim 10, wherein the administration is oral administration.

\* \* \* \* \*